United States Patent [19]

Steinberg et al.

[11] Patent Number: 5,162,332
[45] Date of Patent: Nov. 10, 1992

[54] SELECTED 17 β-POLYAROYL-4-AZA-5 α-ANDROST-1-EN-3-ONES AS STEROIDAL REDUCTASE INHIBITORS

[75] Inventors: Nathan G. Steinberg, Clark; Gary H. Rasmusson, Watchung; Thomas N. Salzmann, North Plainfield, all of N.J.

[73] Assignee: Merck & Co., Inc., Rahway, N.J.

[21] Appl. No.: 773,735

[22] Filed: Oct. 9, 1991

Related U.S. Application Data

[63] Continuation of Ser. No. 540,967, Jun. 20, 1990, abandoned.

[51] Int. Cl.$^5$ .................... A61K 31/58; C07J 73/00
[52] U.S. Cl. ..................................... 514/284; 546/77
[58] Field of Search ........................... 546/77; 514/284

[56] References Cited

U.S. PATENT DOCUMENTS

| | | | |
|---|---|---|---|
| 2,227,876 | 1/1941 | Bolt | 546/77 |
| 3,239,417 | 3/1966 | Tullin et al. | 546/77 |
| 3,264,301 | 8/1966 | Doorenbos et al. | 546/77 |
| 3,285,918 | 11/1966 | Doorenbos et al. | 546/77 |
| 4,220,775 | 9/1980 | Rasmusson et al. | 546/77 |
| 4,317,817 | 3/1982 | Blohm et al. | 424/226 |
| 4,377,584 | 3/1983 | Rasmusson et al. | 546/77 |
| 4,732,897 | 3/1988 | Cainelli et al. | 514/222 |
| 4,760,071 | 7/1988 | Rasmusson et al. | 514/284 |
| 4,845,104 | 7/1989 | Carlin et al. | 514/284 |
| 4,859,681 | 8/1989 | Rasmusson et al. | 514/284 |
| 4,882,319 | 11/1989 | Holt et al. | 514/119 |
| 4,910,226 | 3/1990 | Holt et al. | 514/573 |
| 5,098,908 | 3/1992 | Steinberg et al. | 514/284 |

FOREIGN PATENT DOCUMENTS

| | | |
|---|---|---|
| 970692 | 11/1972 | Canada . |
| 0004949 | 4/1979 | European Pat. Off. . |
| 155096 | 2/1985 | European Pat. Off. . |
| 0314199 | 2/1985 | European Pat. Off. . |
| 0277002 | 1/1988 | European Pat. Off. . |
| 0289327 | 4/1988 | European Pat. Off. . |
| 0343954 | 5/1989 | European Pat. Off. . |
| 0375344 | 12/1989 | European Pat. Off. . |
| 0375345 | 12/1989 | European Pat. Off. . |
| 0375347 | 12/1989 | European Pat. Off. . |
| 0375349 | 12/1989 | European Pat. Off. . |

OTHER PUBLICATIONS

Endo., vol. 91, No. 2 (1972) by Neri, et al.
Steroids, 14, 269 (1969), by Nayfeh, et al.
Endo., vol. 92, p. 1216 (1973) by Voigt & Hsia.
J. Pharm. Sci., 62, 4, pp. 638-640 (1973) by Doorenbos & Solomons.
J. Pharm. Sci., 60, 8, pp. 1234-1235 (1971), by Doorenbos & Brown.
J. Pharm., 63, 4, pp. 620-622 (1974) by Doorenbos & Kim.
J. Med. Chem. (1986) 29 (11): pp. 2298-3115 by Rasmusson, et al.
Prostate (1986) 9 (1): pp. 65-75 by Brooks, et al.
Steroids (1986) 47 (1): pp. 1-19 by Brooks, et al.
Endocr. (1985) 117 (2): pp. 571-579, by Liang, et al.
J. Med. Chem. (1984) 27 (12): pp. 1690-1701, by Rasmusson, et al.
J. Org. Chem. (1981) vol. 46, No. 7, pp. 1442-1446.
Chem. Abstracts, vol. 95, 109055j, by T. Liang, et al.
JNCI, vol. 74, No. 2, pp. 475-481 (Feb. 1985).
The Prostate, vol. 10, pp. 189-197 (1987) by G. L. Andriole, et al.
J. Endocr., vol. 57, pp. 111-121 (1973), by K. D. Bingham, et al.
Toxicol. Appl. Pharmacol., vol. 103, pp. 222-227 (1990), by G. L. Kedderis, et al.
Bioinorganic Chemistry, 17, pp. 372-376 (1986) by B. W. Metcalf, et al.
Biochemistry, 1990, vol. 29, pp. 2815-2824, by M. A. Levy, et al.
J. Med. Chem., 1990, vol. 33, pp. 943-950, D. A. Holt, et al.
J. Steroid Biochem., vol. 34, Nos. 1-6, pp. 571-575 (1989), by M. A. Levy, et al.
J. Med Chem., vol. 33, pp. 937-942 (1990) by D. A. Holt, et al.
TIPS, Dec. 1989, vol. 10, pp. 491-495, by D. W. Metcalf, et al.
Steroids, vol. 35, No. 3 (Mar 1980), pp. 1-7.
Prostate, vol. 9, pp. 311-318, (1986) by N. Stone, et al.
Steroids, vol. 47, No. 1, pp. 1-19 (1986) by J. R. Brooks, et al.
Lancet, Nov. 1986, No. 8515, pp. 1095-1096.
J. Clin. Endocrin. and Metab., vol. 55, No. 1, pp. 188-193 (1987).

*Primary Examiner*—Mukund J. Shah
*Assistant Examiner*—Jyothsna Venkat
*Attorney, Agent, or Firm*—Salvatore C. Mitri; Charles M. Caruso

[57] ABSTRACT

Selected 17β-Polyaroyl-4-aza-5α-androst-1-en-3-ones as steroidal reductase inhibitors of the formula:

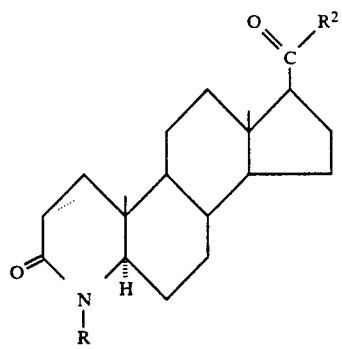

wherein
R is selected from hydrogen, methyl and ethyl
$R^2$ is polycyclic aromatic radical which can be substituted with one or more of: —OH, protected —OH, —OC$_1$—C$_4$ alkyl, C$_1$-C$_4$ alkyl, or nitro, wherein the doted line represents a double bond which can be present, and pharmaceutically acceptable salts or esters thereof, and a pharmaceutical formulation. The above compounds are active as steroidal reductase inhibitors and thus are useful topically for treatment of acne, seborrhea, female hirsutism, and systemically in treatment of benign prostatic hypertrophy.

4 Claims, No Drawings

SELECTED 17 β-POLYAROYL-4-AZA-5 α-ANDROST-1-EN-3-ONES AS STEROIDAL REDUCTASE INHIBITORS

This is a continuation of application Ser. No. 540,967, filed Jun. 20, 1990, now abandoned.

BACKGROUND OF THE INVENTION

The present invention relates to selected 17β-polyaromatic benzoyl-4-aza-5α-androst-1-en-3-ones and related compounds and the use of such compounds as steroidal reductase inhibitors.

DESCRIPTION OF THE PRIOR ART

The literature describes that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal anti-androgens having undesirable hormonal activities of their own. The estrogens, for example, not only counteract the effect of the androgens but have a feminizing effect as well. Non-steroidal anti-androgens have also been developed, for example, 4'-nitro-3'-trifluoromethylisobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfe et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotesterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steriod compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638-640 (1973); Doorenbos and Brown, J. Pharm. Sci., 60 8, pp. 1234-1235 (1971); and Doorenbos and Kim, J. Pharm. Sci. 63, 4, pp. 620-622 (1974).

In addition U.S. Pat. Nos. 4,377,584, 4,220,775, 4,859,681, 4,760,071 and the articles J. Med. Chem. 27, p. 1690-1701 (1984) and J. Med. Chem. 29, 2998-2315 (1986) of Rasmusson et al., U.S. Pat. No. 4,845,104 to Carlin et al. and U.S. Pat. No. 4,732,897 to Cainelli et al. describe 4-aza-17β-substituted-5α-androstan-3-ones which are said to be useful in the treatment of hyperandrogenic conditions. However, none of the cited references suggest that any of the novel 17β-polyaroyl-4-aza-5α-androst-1-en-3-ones of the present invention would have utility as highly potent testosterone-5α-reductase inhibitors.

SUMMARY OF THE INVENTION

The present invention is concerned with novel 17β-polyaroyl-4-aza-5α-androst-1-en-3-ones and related compounds, processes for their preparation, pharmaceutical formulations comprising the novel compounds as active ingredients and methods of inhibiting testosterone-5α-reductase and of treating hyperandrogenic conditions with the novel compounds or their pharmaceutical formulations.

In accordance with the present invention there is provided 17β-polyaroyl-4-aza-5α-androst-1-en-3-one compounds of the formula:

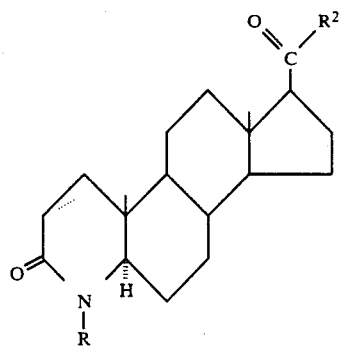

wherein

R is selected from hydrogen, methyl and ethyl, $R^2$ is a polycyclic aromatic radical which can be substituted with one or more of: —OH, protected —OH, $OC_1$-$C_4$ alkyl, $C_1$-$C_4$ alkyl, or nitro, wherein the dotted line represents a double bond which can be present, and pharmaceutically acceptable salts or esters thereof.

Preferred embodiments of the novel compounds of our invention are represented by the formula:

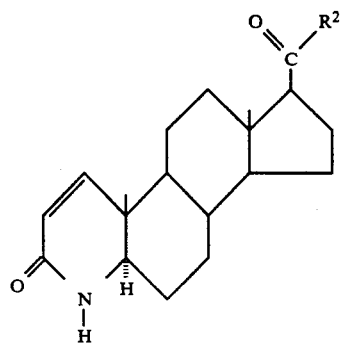

wherein

R is hydrogen, methyl or ethyl, and $R^2$ is phenyl substituted with one or more phenyl groups on the 2, 3, 4 or 5 positions of the phenyl ring.

By the term "polyaroyl" is meant an aryl ketone containing more than 1 aryl ring, either fused or at a substituent. Examples are biphenyl, naphthyl, anthracyl, phenanthryl, and the like.

Representative compounds of the present invention include the following:

17β-(4-biphenyl)-4-aza-5α-androst-1-en-3-one:
17β-(3-biphenyl)-4-aza-5α-androst-1-en-3-one;
17β-(1-naphthyl)-4-aza-5α-androst-1-en-3-one;
17β-(2-naphthyl)-4-aza-5α-androst-1-en-3-one;
17β-(1-phenanthryl)-4-aza-5α-androst-1-en-3-one;
17β-(2-phenanthryl)-4-aza-5α-androst-1-en-3-one;
17β-(1-biphenyl)-4-aza-5α-androst-1-en-3-one;
17β-(9-anthracyl)-4-aza-5α-androst-1-en-3-one;
and the corresponding compounds wherein the 4-hydrogen substituent is replaced in each of the above-named compounds by a methyl or an ethyl radical.

Also included within the scope of this invention are pharmaceutically acceptable salts or esters, where a basic or acidic group is present on the polyaroyl moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl and the like, and these esters known in the art for modifying solubility or hydrolysis characteristics for use as sustained release or prodrug formulations.

The novel compounds of formula I of the present invention are prepared by a method starting with the known steroid ester of the formula:

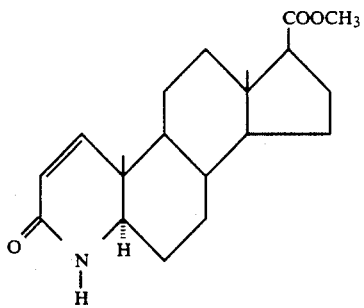

which includes the stages of (1) dehydrogenating said starting material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. For the dehydrogenation step, it is preferable that the 4-aza nitrogen be unsubstituted. The dehydrogenation step can be carried out, e.g., according to the procedure of Dolling, et al, involving dichlorodicyanobenzoquinone, JACS (1988), Vol. 110, pp. 3318–3319. Stage (2) may consist of one or more chemical steps and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneseleninic anhydride in refluxing chlorobenzene to form a 17β-alkoxycarbonyl-4-aza-5α-androst-1-en-3-one (IV), (2) the formed 5α-androst-1-en-3-one compound from step (1) is reacted with sodium hydride and under anhydrous conditions in a neutral solvent such as dimethylformamide, (2) contacting the resulting reaction mixture with an alkyl (methyl or ethyl) iodide to form the corresponding 17β-alkoxycarbonyl-4-alkyl-4-aza-5α-androst-1-en-3-one (V), (3) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy-4-alkyl-4-aza-5α-androst-1-en-3-one (VI), (4) said steroidal acid is then converted to its corresponding 2-thiopyridyl ester by refluxing with triphenyl phosphine and 2,2'-dipyridyl disulfide in an inert solvent and the product 17β-(2-pyridylthiocarbonyl)-4-alkyl-4-aza-5α-androst-1-en-3-one (VII) is isolated by chromatography on silica, (5) said pyridylthio ester is then reacted with an $R^2$-Li or an $R^2$MgX (X=Cl, Br) compound such as p-biphenylmagnesium chloride in tetrahydrofuran to form the desired product 17β-(p-biphenylylcarbonyl)-4-alkyl-4-aza-5α-androst-1-en-3-one (VIII) which is isolated by chromatography on silica gel.

For example, where $R^2$ is p-hydroxybiphenyl, this can be derived by starting with an appropriate bromobiphenylphenol, e.g. p-bromobiphenylphenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

By the term "$C_1$-$C_4$ alkyl" is used herein, is meant linear or branched alkyl, including methyl, ethyl, propyl, isopropyl, n-butyl, isobutyl, sec-butyl and t-butyl.

In accordance with the process of our invention, the corresponding 17β-polyaroyl-4-aza-5α-androst-1-en-3-one XV is readily prepared from the 17β(alkoxycarbonyl)-4-aza-5α-androsten-3-one (IV) by repeating the above series of reaction steps but omitting step 2 hereinabove, i.e., treatment of the 4-aza-5α-androst-1-en-3-one with sodium amide followed by methyl or ethyl iodide.

In accordance with a further alternate process of preparing the compounds of our invention, having only hydrogen as the sole substituent on the ring A-nitrogen, the double bond in the A-ring is introduced as the last step of the process. Thus, a 17β-alkoxycarbonyl-4-aza-5α-androstan-3-one (III) is hydrolyzed to the corresponding steroidal acid, 17β-carboxy-4-aza-5α-androstan-3-one, (IX) which, in turn, is converted to the corresponding thio-pyridyl ester, 17β-(2-pyridylthiocarbonyl)-4-aza-5α-androstan-1-one (X) followed by treatment of the ester with an $R^2$MgX or $R^2$Li compound wherein $R^2$ is as defined hereinabove to form a 17β-

(polyaromatic benzoyl)-4-aza-5α-androstan-3-one (XI) which is dehydrogenated as previously described to produce compound XIV, 17β-(acyl)-4-aza-5α-androst-1-en-3-one.

The above reactions are schematically represented in the following flowsheet:

FLOWSHEET

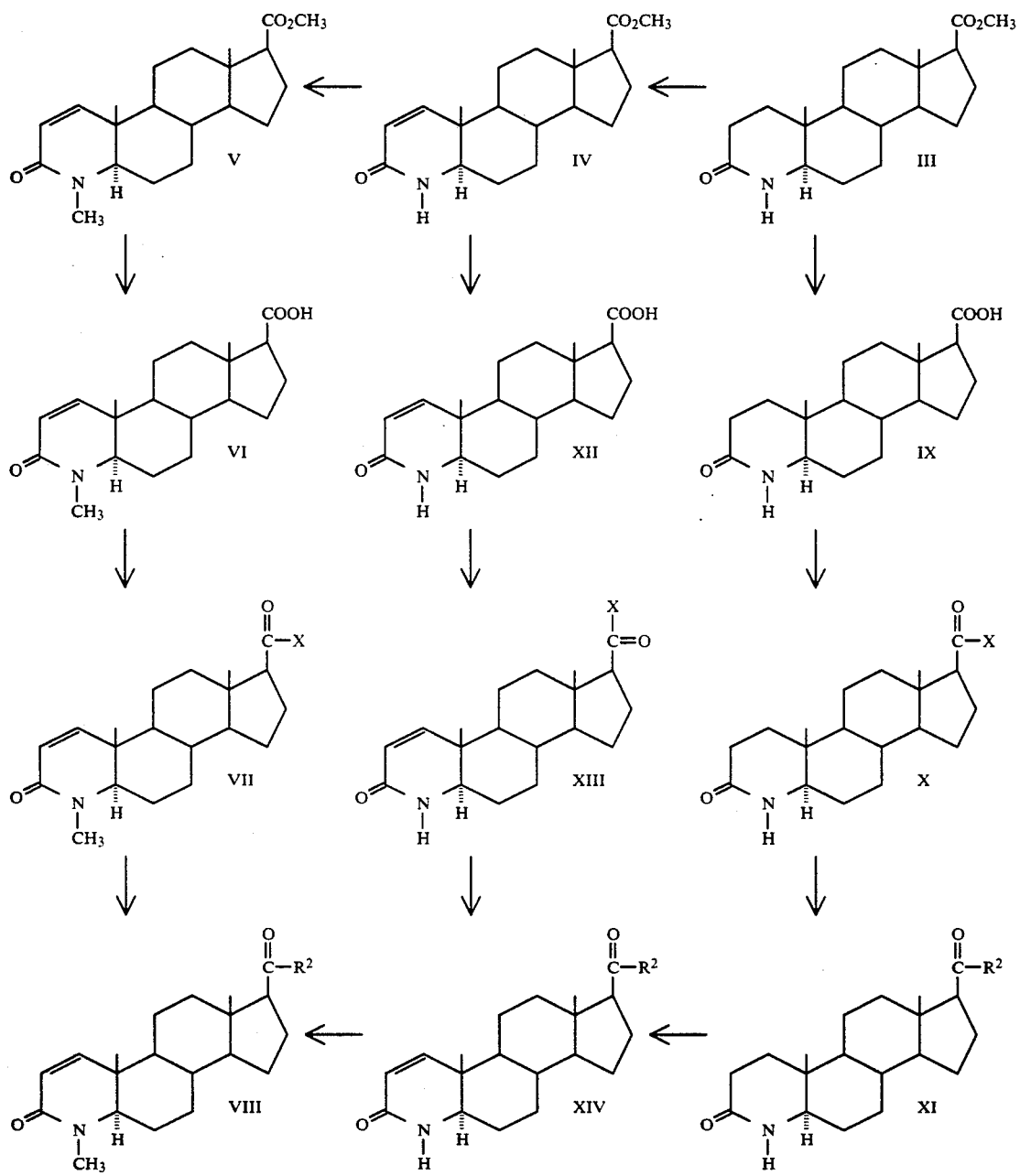

X is 2-pyridylthio or 1-benzotriazoloxy

Also, within the scope of the present invention are ketone reduction products of the formula:

wherein X is a 2-thiopyridylcarbonyl substituent and $R^2$ is defined as hereinabove.

The compounds of the present invention, prepared in accordance with the method described above, are, as already described, potent antiandrogens by virtue of their ability to specifically inhibit testosterone-5α-reductase.

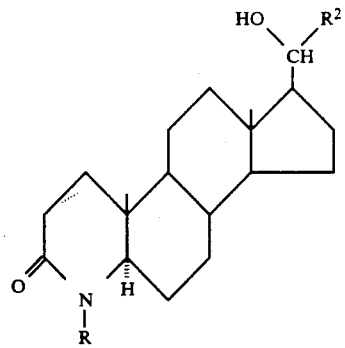

wherein

R is selected from hydrogen, methyl and ethyl $R^2$ is a polycyclic aromatic radical which can be substituted with one or more of: —OH, protected —OH, —OC$_1$–C$_4$ alkyl, C$_1$–C$_4$ alkyl, or nitro, wherein the dotted line represents a double bond which can be present, and pharmaceutically acceptable salts or esters thereof, and a pharmaceutical formulation.

These compounds can be made by conventional sodium borohydride reduction of the carbonyl attached to $R^2$ without reducing the amide carbonyl in Ring A or the 1,2-double bond, if present. If the $R^2$ phenyl contains a carbonyl function, it can be selectively blocked and then regenerated after the borohydride reduction by conventional methods.

The borohydride reduction can be carried out in, e.g. water or aqueous methanol, at a temperature of room temperature to 50° C. and the product then isolated and purified by conventional means. The compounds are also active as 5-alpha reductase inhibitors.

Accordingly, the present invention is particularly concerned with providing a method of treating the hyperandrogenic conditions of acne vulgaris, seborrhea, and female hirsutism by topical administration, and a method of treating all of the above conditions as well as benign prostatic hypertrophy, by oral or parenteral administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The method of preparing the novel 17β-polyaroyl compounds of the present invention, already described above in general terms, may be further illustrated by the following examples.

EXAMPLE 1

Methyl 3-oxo-4-aza-5α-androst-1-ene-17β-carboxylate

A suspension of 83.7 g of methyl 3-oxo-aza-5α-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous NaHCO$_3$ solution and saturated NaCl solution, then dried and evaporated to leave 172.4 g. This material was chromatographed on 2.56 kg of silica gel eluting first with dichloromethane (5 liters) and then with 4:1 dichloromethane-acetone. The desired product was eluted with 8 liters of the above-mixed solvent and evaporated to dryness in vacuo to yield 53.4 g solid. It was washed with diethyl ether and dried to leave 49.5 g of the above-titled product, m.p. 278°–280° C.

*Rasmusson Johnston and Arth. U.S. Pat. No. 4,377,584, Mar. 22, 1983.

EXAMPLE 2

S-(2-Pyridyl)-3-oxo-4-aza-5α-androst-1-ene-17β-thiocarboxylate

A suspension of 25 g of the product of Example 1 in 125 ml of methanol was treated with a solution of KOH (12.5 g) in 12.5 ml of water. After refluxing for 4 hours, the solution was acidified with 6 NHCl and then was diluted with water. The crude acid (23.32 g) was separated, dried and had m.p. 300° C.

The crude, dry acid (23 g), triphenylphosphine (36.45 g) and 2,2'-dipyridyldisulfide (30.4 g) were suspended in 138 ml of toluene with stirring for 3 hours at room temperature. The reaction mixture was directly chromatographed on a column of 4.5 kg of silica gel eluting with 9:1 ethyl acetate-acetone to give 20.4 g of the desired product, m.p. 218°-220° C.

EXAMPLE 3

Synthesis of 17-β-(4Phenylbenzoyl)-4-aza-5α-androst-1-en-3-one

To a suspension of 258.0 mg of dry activated magnesium chips in 5.0 ml of dry THF was added 932.0 mg of 4-bromobiphenyl in 5.0 ml of dry THF under $N_2$. The reaction was run in an ultrasonic bath at a temperature range of 24°-30° C. To the well-agitated mixture was added dropwise 30 μl of 1,2-dibromoethane/$N_2$. The reaction was allowed to proceed for 1-1½ hours at 28° C./$N_2$. The concentration of the Grignard reagent was 4.0 mmoles in 10.0 ml of dry THF.

The steroid from Example 2 (205.0 mg of thiopyridyl ester) was suspended in 2.0 ml of dry THF, cooled to −80° C. and the above Grignard 3.80 ml (3 equivalents) was added via syringe to the steroidal suspension over 5-10 minutes/$N_2$. The reaction was allowed to proceed for 1 hour at −80° C./$N_2$ and then at −10° C. for an additional hour/$N_2$. The solution was diluted with 10.0 ml of methylene chloride and quenched with saturated aqueous solution of $NH_4Cl$ to pH=4. The organic layers were separated, washed 3 times with water, 3 times with saturated sodium chloride, dried over $MgSO_4$, filtered, and evaporated under vacuum to afford 156.2 mg of crude product. Crystallization from EtOAc gave the above-titled product in 98.58 mg, m.pt. 290° C.-290.5° C.

Anald. Calcd. for $C_{31}H_{35}NO_2$; C,82.08; H,7.78; N,3.09; Found: C,81.84; H,8.01; N,3.06.

FAB: Calc. for $C_{31}H_{35}NO_2$: 453; Found: 453.

EXAMPLE 4

17-β-(3-Phenylbenzoyl)-4-aza-5α-androst-1-en-3-one

To a suspension of 258.0 mg of dry activated magnesium chips in 8.0 ml of dry THF was added 932.0 mg of 3-bromobiphenyl in 2.0 ml of dry THF under $N_2$. The reaction was run in an ultrasonic bath at a temperature range of 24°-30° C. To the well-agitated mixture was added dropwise 30 μl of 1,2-dibromoethane/$N_2$. The concentration of the Grignard reagent was 4 mmoles in 10.0 ml of dry THF.

The steroid from Example 2, 205.0 mg (0.5 mmoles) was suspended in 2.0 ml of dry THF, cooled to −80° C. and the above Grignard 3.80 ml (3 equivalents) was added via syringe to the steroidal suspension over 5-10 minutes/$N_2$. The reaction was allowed to proceed for 1 hour at −80° C./$N_2$ and then at −10° C. for an additional hour/$N_2$. The solution was diluted with 10.0 ml of methylene chloride and quenched with a saturated aqueous solution of $NH_4Cl$ to pH=4. The organic layers were separated, washed 3 times with water, 3 times with saturated sodium chloride, dried over $MgSO_4$, filtered, and evaporated under vacuum. Crystallization from ethyl acetate afforded 122.84 mg of product. The material was purified on 20.0 g of silica gel column using 70:30 ($CHCl_3$-acetone) as eluant, to give a single spot material 117.0 mg of the above-titled compound, m.pt. 184°-185° C.

Anald. Calcd. for $C_{31}H_{35}NO_2$; C,82.08; H,7.78; N,3.09; Found: C,82.28; H,8.04; N,2.98.

FAB: Calcd. for $C_{31}H_{35}NO_2$: 453; Found: 453.

We claim:

1. A compound of the formula:

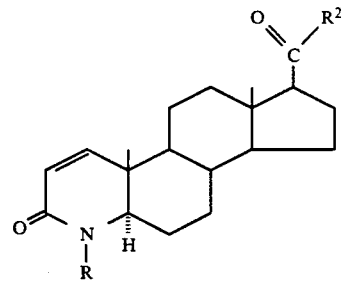

wherein

R is selected from hydrogen, methyl and ethyl and $R^2$ is a polycyclic aromatic radical which can be substituted with —OH, protected —OH, —OC-$_1$-C$_4$ alkyl, C$_1$-C$_4$ alkyl, halo or nitro, said polycyclic aromatic radical being a member selected from the group consisting of 4-biphenyl, 3-biphenyl, naphthyl, anthracyl, or phenanthryl.

2. The compound of claim 1 wherein the compound is:

17β(4-phenylbenzoyl)-4-aza-5α-androst-1-en-3-one;

17β(3-phenylbenzoyl)-4-aza-5α-androst-1-en-3-one;

and the corresponding compounds wherein the 4-hydrogen substituent is replaced in each of the above named compounds by a methyl or an ethyl radical.

3. A method of treating the hyperandrogenic condition of acne vulgaris, seborrhea, female hirsutism, and benign prostatic hypertrophy comprising parenteral administration to a patient in need of such treatment of a therapeutically effective amount of a compound of formula:

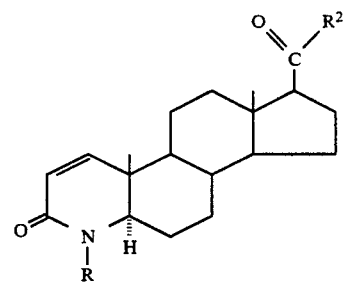

wherein

R is selected from hydrogen, methyl and ethyl, and $R^2$ is a polycyclic aromatic radical which can be substituted with —OH, protected —OH, —OC-$_1$-C$_4$ alkyl, C$_1$-C$_4$ alkyl, halo or nitro, said polycyclic aromatic radical being a member selected from the group consisting of 4-biphenyl, 3-biphenyl, naphthyl, anthracyl, or phenanthryl.

4. A pharmaceutical composition comprising a pharmaceutically acceptable carrier and a therapeutically effective amount of the compound of claim 1.

* * * * *